US010630678B2

(12) United States Patent
Kermani (10) Patent No.: US 10,630,678 B2
(45) Date of Patent: Apr. 21, 2020

(54) METHOD AND APPARATUS FOR DNA-BASED AUTHENTICATION SYSTEM

(71) Applicant: Bahram Ghaffarzadeh Kermani, Los Altos, CA (US)

(72) Inventor: Bahram Ghaffarzadeh Kermani, Los Altos, CA (US)

(*) Notice: Subject to any disclaimer, the term of this patent is extended or adjusted under 35 U.S.C. 154(b) by 1157 days.

(21) Appl. No.: 14/857,764

(22) Filed: Sep. 17, 2015

(65) Prior Publication Data
US 2016/0080384 A1    Mar. 17, 2016

Related U.S. Application Data

(60) Provisional application No. 62/051,941, filed on Sep. 17, 2014.

(51) Int. Cl.
*H04L 29/06* (2006.01)
*G16B 30/00* (2019.01)

(52) U.S. Cl.
CPC .......... *H04L 63/0861* (2013.01); *G16B 30/00* (2019.02)

(58) Field of Classification Search
None
See application file for complete search history.

(56) References Cited

U.S. PATENT DOCUMENTS 6,312,911 B1* 11/2001 Bancroft ................ B82Y 10/00
                                                      435/6.11
8,392,965 B2*  3/2013 Carter .................... G06F 21/34
                                                      382/115
2002/0129251 A1*  9/2002 Itakura ............ G06K 19/06037
                                                      713/176
2005/0267971 A1* 12/2005 Fritz ................. H04L 29/12132
                                                      709/225

OTHER PUBLICATIONS

Hashiyada "DNA Biometrics" Biometrics. InTech, pp. 139-154 (Year: 2011).*
Srivastava et al. I.J. Fingerprints, Iris and DNA Features based Multimodal Systems: A Review. Information Technology and Computer Science Jan. 2013, 02, pp. 88-111 (Year: 2013).*
Shendure et al. Next-generation DNA sequencing. Nature Biotechnology. vol. 26, No. 10, pp. 1135-1145 (Year: 2008).*
Hashiyada. Development of Biometric DNA Ink for Authentication Security. Tohoku J. Exp. Med., vol. 204, pp. 109-117 (Year: 2004).*
Gao. A Few DNA-based Security Techniques. 2011 IEEE Long Island Systems, Applications and Technology Conference, pp. 1-5. IEEE 2011 (Year: 2011).*
Clement et al. The GNUMAP algorithm: unbiased probabilistic mapping of oligonucleotides from next-generation sequencing. Bioinformatics, vol. 26, Issue 1, pp. 38-45 (Year: 2010).*

* cited by examiner

*Primary Examiner* — Olivia M. Wise (57) ABSTRACT

Techniques for biochemcally-enabled security/authentication mechanisms are described herein. In an example embodiment, a security system receives a biological sample from a key. The biological sample includes a set of deoxyribonucleic acid (DNA) oligos that represent a code assigned to the key. The set of DNA oligos is sequenced to obtain a set of read sequences. The set of read sequences is then filtered to identify a set of filtered sequences. The set of filtered sequences is matched to sets of expected sequences, where the sets of expected sequences are assigned to respective keys issued for the security system. Access to a resource is then granted or denied based on whether the set of filtered sequences matches with any set from the sets of expected sequences.

20 Claims, 7 Drawing Sheets

METHOD AND APPARATUS FOR DNA-BASED AUTHENTICATION SYSTEM

PRIORITY

This application claims the priority and benefit of U.S. Provisional Application No. 62/051,941, filed on Sep. 17, 2014, the entire content of which is incorporated by reference herein.

TECHNICAL FIELD

This disclosure generally relates biochemically-enabled and electrochemically-enabled security mechanisms.

BACKGROUND

Conventional security mechanisms invariably use only mechanical, electrical/electronic, or biometric elements to provide secure access in security contexts. For example, a typical mechanical security mechanism uses a key-lock system, in which only a key matched to a lock would provide access through a locked door. A typical electronic security mechanism uses a password-protected system, in which a user must type the correct password in order to gain access to the system. A typical biometric security mechanism uses a fingerprint-protected system, which scans a user's fingerprint and grants access only if the scanned fingerprint matches the fingerprint of an authorized user. While each of the mechanical, electrical/electronic, and biometric security mechanisms has its own advantages in certain security contexts, the ever-continuing advancement of technology creates the need for new and improved security mechanisms for existing, as well as emerging security contexts.

DETAILED DESCRIPTION

The following description sets forth numerous specific details such as examples of specific systems, components, methods, and so forth, in order to provide a good understanding of various embodiments of the techniques described herein for chemically-enabled security. It will be apparent to one skilled in the art, however, that at least some embodiments may be practiced without these specific details. In other instances, well-known components, elements, or methods are not described in detail or are presented in a simple block diagram format in order to avoid unnecessarily obscuring the techniques described herein. Thus, the specific details set forth hereinafter are merely exemplary. Particular implementations may vary from these exemplary details and still be contemplated to be within the spirit and scope of the present invention.

Reference in the description to "an embodiment", "one embodiment", "an example embodiment", "some embodiments", and "various embodiments" means that a particular feature, structure, or characteristic described in connection with the embodiment(s) is included in at least one embodiment of the invention. Further, the appearances of the phrases "an embodiment", "one embodiment", "an example embodiment", "some embodiments", and "various embodiments" in various places in the description do not necessarily all refer to the same embodiment(s).

The description includes references to the accompanying drawings, which form a part of the detailed description. The drawings show illustrations in accordance with exemplary embodiments. These embodiments, which may also be referred to herein as "examples," are described in enough detail to enable those skilled in the art to practice the embodiments of the claimed subject matter described herein. The embodiments may be combined, other embodiments may be utilized, or structural, logical, and other changes may be made without departing from the scope and spirit of the claimed subject matter. It should be understood that the embodiments described herein are not intended to limit the scope of the subject matter but rather to enable one skilled in the art to practice, make, and/or use the subject matter.

Biochemically-Enabled and Electrochemically-Enabled Security

Described herein are various embodiments of techniques for bio/electro/chemically-enabled security. In some embodiments, a receptacle is configured to receive a key and to obtain a biological or chemical sample from the key. The key contains biological or chemical material in which a code is encoded via an electrochemical or biochemical element. Some examples of electrochemical and biochemical encoding elements include, without limitation:

1. Deoxyribonucleic acid (DNA) or another nucleic acid;
2. A chemical material which has a certain pH;
3. A liquid material that can maintain a certain electrical charge.

The key is a physical device that may or may not be similar to a conventional key (e.g., such as a key having bittings on the blade). Preferably, DNA is utilized as the biochemical element. In an example embodiment, the key resembles a conventional key except that it includes a microfluid chamber containing biological material. Once the key is successfully inserted into a receptacle/lock, the key is able to inject a small sample amount of the biological material into a receptor that is available in the lock. The receptor receives the injected sample, in this case DNA material in the form of a solution of oligonucleotide molecules (also referred to as just oligonucleotides, or oligos). Following this step, DNA sequencing can be done on the DNA oligos. Without a loss of generality, the DNA sequencing in this application includes all the steps of sample/library preparation, including but not limited to enrichment, purification, elution, and amplification. For sequencing to be done, the deposited biochemical sample is transferred to a sequencing unit. This operation can be done by a user or automatically by a machine. Alternatively, the DNA sequencing can be done in-place, for example if the receptacle/lock is equipped with a suitable sequencing system. It must be noted that although DNA sequencing is the method of choice for some embodiments, other ways of reading a signal from DNA oligos, such as DNA microarrays, could also be utilized. DNA microarrays are often hybridization based, and have specific interrogation sites. Without loss of generality, throughout the present description the term "DNA sequencing" is used as an example representing a signal acquisition method for acquiring signals/data from biochemical and/or electrochemical samples. After DNA sequencing is complete, signal/data representing one or more properties of the injected sample is acquired and processed. The acquired signal/data is then used to control access to a given resource. For example, secure access to one or more resources is granted if the acquired signal/data matches (or otherwise conforms) to a security profile that controls access to the one or more resources. Conversely, if the acquired signal/data does not match (or otherwise does not conform) to the security profile, then access to the one or more resources is denied.

A security mechanism in accordance with the techniques described herein may have different applications and usages. In some embodiments, examples of usage for the DNA keys described herein would be for controlling access to safe deposit boxes at banks and other financial institutions, where extra high security is needed and a slight delay due to the signal/data acquisitions and reading may be tolerated.

In some embodiments, security mechanisms that use non-DNA encoding elements may be faster (e.g., such as mechanisms that read the electrical charge or pH of a sample containing electrochemical encoding element), and therefore could be used for other types of keys, although they likely will not be as secure as the DNA counterparts due to the limited search space they provide. For instance, a pH reader or an electrical charge reader (for conventional use) may give only 10 levels of identification. In comparison, a DNA sequence could easily provide billions of levels of identification. Without loss of generality, for the rest of the present description DNA-based security mechanisms will be discussed. It is noted, however, that DNA-based security mechanisms are also expected to get faster, especially with the advent of fast portable sequencing machines.

In some embodiments, codes can be transferred/stored in a key in the form of oligos having one or more DNA or RNA nucleic acid sequences. A nucleic acid sequence (also referred to as just "sequence") is a succession of discrete data units that indicate the order of nucleotide bases within a DNA or RNA oligo molecule; for example, in a strand of DNA or RNA oligo, "A" is typically used to indicate an adenine base, "G" is typically used to indicate a guanine base, "C" is typically used to indicate a cytosine base, "T" is typically used to indicate a thymine base (for DNA only), and "U" is typically used to indicate an uracil base (for RNA only). Each oligo represents $4^N$ discrete units of information, where N is the length (in number of bases) of the oligo. For instance, for N=10, there would be approximately ~1000 billion discrete units of information that can be encoded in a 10-mer (e.g., an oligo with length 10). Oligos with length 80 (80-mers) and above are routinely synthesized with high quality, using state-of-the-art DNA synthesizer systems. Thus, an oligo with length $4^{80}$ provides approximately ~$1.5*10^{48}$ discrete codes. This means that if 1000 billion keys are defined for every person in the world, then the codes stored in such keys are still $2*10^{26}$ unique. Consequently, codes encoded in oligos with length much less than N=80 are sufficient to fully enable the security mechanisms in accordance with the techniques described herein. For example, if oligos with length N=37 are used, then 2700 billion keys can be made for every person in the world.

In order to increase the security of the system, in some embodiments more than one sequence can be specified to and associated with each key. This scheme loses power (of uniqueness) only linearly, and therefore the exponential power of the search space remains very strong. For instance, if every key is made using M different sequences, then the number of unique keys that can be made would be $$\frac{4^N}{M}.$$

Ordinarily, M does not have to be large—e.g., M=10 would be a reasonable number.

One advantage of the herein-described biochemical security mechanisms (over mechanical, electrical/electronic, and biometric security mechanisms) is that a person him/herself can make any combination of the DNA keys described herein. For instance, suppose that 4 banks have provided a user with 5 different DNA keys, each. Normally, the solution with the DNA oligos for each key is provided with its own DNA tube (to be used for filling the keys). This is due to the fact that since a DNA oligo solution is a consumable material, then it will have a limited lifetime, e.g., 1000 uses, or 30 years, etc. If the solutions (tubes etc.) are made available to the user, the user may also want to make (e.g., fill) a bank-specific key from all the 5 keys of a specific bank without losing any operability of the original 5 keys. Alternatively, the user can mix the DNA solutions for some or all of the 20 keys in any combination s/he would like without losing any operability of the combined keys. For example, the user may want to combine the DNA oligo solutions for all the 20 keys into a single master-key. In that case, the user would pool an amount from all the tubes into a single pool, and then fill the master-key with the pooled DNA solution.

According to the techniques described herein, the process of making master-keys is therefore very simple. The user can simply combine an amount from the DNA solution for each of the keys with those of the other keys. Then, the combined solution is inserted into a single physical key. This key will then act as a master-key for all of its components' codes. For example, the user can use this master-key in any of the 4 banks for any of the secure accesses associated with any of the 5 keys from each bank. (It is also noted that the operation of combining the DNA solutions for the issued keys may be performed by the user, or alternatively may be performed by the bank or another institution.)

In order to prevent abuse and to reduce the possibility for security breach, in some embodiments the maximum number of keys that can be combined into a master-key can be limited. This limitation can be fully controlled and enabled by parameters of the decoding mechanism used by the underlying security system. For example, in some embodiments the decoding mechanism for a master-key may works as described below. Suppose that a key used by a user at a given security system is a master-key with K (K>1) keys multiplexed (as described heretofore), where each multiplexed key has M (M>1) separate codes encoded in its DNA oligos. After a biochemical sample from the key is injected for analysis into the system, the following operations may be performed to determine whether the presented master-key is valid:

1. The DNA oligos that exist in the sample received from the master-key are read by a DNA sequencer. For a master-key with the above specifications, there should be M*K clusters of sequences, with each cluster possibly having a count Ni (i=1 ... M*K) sequences in it. If the DNA solution in the master-key is uniform, then all the Ni values should be roughly similar. This heuristic can, therefore, be used to check the validity of the data acquired by sequencing the DNA oligos in the injected sample. For instance, the ratio of Ni to Nj for any combination of "i" and "j" should be less than 2.

2. Each Ni count value should be more than a specified threshold in order to obtain immunity to noise. This threshold could also be used to filter out sequences that were read incorrectly. For example, if there are two codes—one with count N1=1000 and the other with count N2=22, and if the threshold is 100, then it can be concluded that only count N1 is valid (while count N2 is not). In other words, only the code corresponding to N1 is valid.

3. The total number of valid sequences (valid Ni's) could then be limited to a certain threshold. For instance, there could be only a mixture of up to 200 keys allowed in the master-key. That is, if more than 200 valid Ni are detected, then the master-key would be determined as invalid.

Example Decoding Mechanism

In accordance with the techniques described herein, in some embodiments a security system may use the following decoding mechanism to determine whether to grant or deny access to a resource when presented with a DNA key.

1. After a biochemical sample from the DNA key is injected for analysis into the system, a DNA sequencer sequences all the DNA oligos detected in the sample.

2. The sequences represented in the DNA oligos may or may not have error detection and/or error correction codes designed into their structure. If error detection/correction codes are included in the DNA oligos during encoding, then such detection/correction can be used to detect/correct errors in the acquired sequences.

3. The set of read sequences (RS) acquired from the DNA key are filtered. In one embodiment, for filtering, the read sequences are binned, and the most frequent bins are identified/filtered based on their counts (e.g., by using a threshold similar to the threshold described above for the master-key decoding mechanism). The set of filtered sequences (FS) in the most frequent bins are then moved to the next step. The filtering operation could be implicit, e.g., by not entering the sequences with many errors into the main computation. Also, the filtering operation may be done by the sequencing instrument, e.g., by suppressing the spots/reads that are not informative or manifest high errors.

4. The set of FS is compared with the sets of sequences associated with the keys issued in the system in order to determine whether the filtered sequences represent a valid key. In some embodiments the set of RS may be used in this comparison step. Also, various comparison mechanisms can be used in this step. In a simple case of 1-key (a one-code key, no master-key), the expected codes for each key are compared to the set of FS or RS (FS/RS), and if a match is found the presented DNA key is determined as valid. The code for each issued key can be defined as a set of expected sequences (ES) associated with that key, and the search space of the system can be defined as a superset including all sets of ES. To determine whether the presented DNA key is valid, the search space is searched for a match between any set of ES and the set of FS/RS that represents the presented DNA key. Ideally, a match is found for only one key, and the set of ES for that key is exactly equal to the set of FS/RS. In some embodiments, however, a different comparison mechanism may determine a successful validation when a given set of ES (from the search space) is found to be a subset of the set of FS/RS. In some embodiments, the decoding mechanism can be configured to allow for a percent of impurity. For example, the impurity may be defined as abs(RS−ES)/RS, where "abs" represents the absolute value operation. If there are 3 keys multiplexed, the size of the set of RS is 3 times the size of the set of ES, and therefore, the impurity that should be tolerated is (3ES−ES)/3ES=(3−1)/3=2/3 or ~67%. For a master-key multiplexing scheme of 20 keys, an impurity of up to (20−1)/20=19/20 or 95% should be tolerated.

5. If in the previous step the presented DNA key is found to be valid, then access to the requested resource is granted; otherwise, access to the resource is denied.

Example Encoding Mechanism

In accordance with the techniques described herein, in some embodiments the following encoding mechanism may be used to design the sequences in the DNA oligos for a key in a security system.

1. During a design phase, a code (e.g., a set of DNA sequences) is assigned to the key, e.g., three sequences at 80 bases each, or 3×80-mers. At this phase, error detection and/or error correction codes may also be designed into the structure of the sequences associated with the key. Such error detection/correction codes may be included in order to provide for detecting/correcting errors that may occur during DNA sequencing.

2. Each of the sequences in the set (e.g., each of the three 80-mers) is then synthesized using a DNA synthesizer system into a DNA oligo.

3. The resulting DNA oligos are then mixed into a DNA solution that represents the code assigned to the key. This step can be performed at the institution issuing the key (e.g., a bank or other financial institution), or at separate institution (e.g., biochemical lab). Alternatively, in some embodiments the synthesized DNA oligos may be provided to the user in suitable containers (e.g., tubes etc.) with instructions for the user on how to mix the oligos on his/her own into a DNA solution for the key.

4. The DNA solution is then transferred (e.g., injected) into a microfluid chamber of the key.

5. When the DNA solution reaches a certain minimum in the key, an indicator (e.g., a marker on the microfluid chamber thereof) can make the user aware of the need to refill the key. Since minute amounts of DNA material is needed for DNA sequencing, it is possible to design keys that are good for millions of uses, and therefore avoid the need for a refill.

Extra Security

In order to increase the security of a DNA key, some embodiments may use a biochemically-encoded ("wet") password. For example, during the design phase of the key, a user can be prompted to provide a password. This password is designed as (or converted into) a sequence that has a look-up length equivalent to the lengths of the code sequences associated with the key. The sequence representing the password is then associated with the key, and is synthesized into a DNA oligo in the same way as the set of code sequences associated with the key. In addition, at the time of decoding the sequence representing the password is added as an additional expected sequence (ES) into the set of ES for the key. In various implementations, the user can be provided with a password, or the user can choose his/her own password. In the latter case, the institution will synthesize and deliver to the user the DNA oligo corresponding to the password (or a set of passwords) as well. The sequence corresponding to the password may then be added to all the keys of the user. (In the event of multiple passwords, all the corresponding sequences may be added to the key.) During decoding, the sample-processing device would first try to find a match in the set of read sequences (RS) acquired from a sample in the key to the particular sequence(s) that correspond to the user's password(s). If a match to the password sequence(s) is not found in the set of RS, then the decoding mechanism would not need to proceed further (i.e., it can consider the key invalid). If such a match is found, then password sequence(s) are removed from the set of RS acquired from the key, and the rest of the decoding mechanism proceeds as described heretofore.

Alternatively, in some embodiments the user's password could be similar to an electronic password that is selected by the user or the institution issuing the DNA key. In these embodiments, the password (or any sequence corresponding thereof) is not inserted/mixed into the DNA solution for the key. Rather, the institution that issues the key (e.g., bank) is aware of this password option and, when requesting access based on the DNA key, the user is asked to enter/type this password as the first check similarly to what is currently done with electronic passwords. If the user passes this first check, then the security system can proceed with decoding the biochemically-encoded DNA key as described heretofore. Alternatively, the regular password can be offered after the validation of the "wet" password. As an additional security measure, in some embodiments the same (or different) electronic password may also be converted into a DNA sequence that is combined with the sequences corresponding to the "wet" password for the key (e.g., with the password sequence(s) embedded in the DNA solution for the key). In some embodiments, extra security can also be obtained by using biometric measurements, such as fingerprints and retina scanning, in a similar manner as the use of an electronic password as described heretofore.

Using Genome Sequences for DNA Keys

As discussed heretofore, in some embodiments the sets of sequences assigned to DNA keys may be random sequences of a certain length. In other embodiments, however, the set of sequences assigned to a DNA key can be derived from the genome of the user to which the DNA key is issued (or genome of other individuals, e.g., relatives, or species, e.g., pets). For example, the genome of the user may be wholly or partially sequenced, and sequences from highly variable portions (e.g., with respect to the entire human population) of certain chromosomes may be used to derive the set of sequences assigned to the DNA key of the user. This, in effect, ensures that the user is the source for his/her DNA key. This provides not only extra security but also extremely high personalization of the DNA keys issued by an institution to its users.

Alternative Method for Biochemically-Enabled Decoding

In an alternative security mechanism, in some embodiments a customer and a key-issuing institution can each have biological elements (e.g., such DNA oligos, RNA oligos, ligase, etc.) that interact during the process of verifying the DNA key of the customer. For instance, the DNA key of the customer can store therein multiple sets of DNA oligos, possibly in addition to the DNA oligos that represent the sequences assigned to the key. Correspondingly, the key-issuing institution can have ligase that can cause fusion of (at least some) of the DNA oligos carried within the customer key. When the customer presents his/her DNA key to request access to a resource (e.g., a deposit box), the security system at the institution would extract a biological sample from the customer key and would apply the corresponding ligase thereto. The resultant biochemical product can be used to trigger an event, such as making a longer DNA oligo product. Then, this resultant product can cause either a flag getting set during decoding or some other event to happen (which could also be as a result of the flag being set). An example of this would be a sequencing system, which in addition to performing DNA sequencing would also report the length of the sequenced DNA oligos (e.g., the length of each acquired and read sequence). If the ligation between the DNA oligos of the customer's DNA key has happened, the read sequences are expected to be longer (e.g., for 2× fusion) and yet longer (e.g., for 3× fusion and more) albeit lower frequency. The lengths and the relationship between the lengths can then be used to set a flag and/or cause another event in order to indicate whether the DNA oligos for the DNA key are valid or not, thereby providing an extra layer of verification and security.

Example System Implementations

Figure 1:
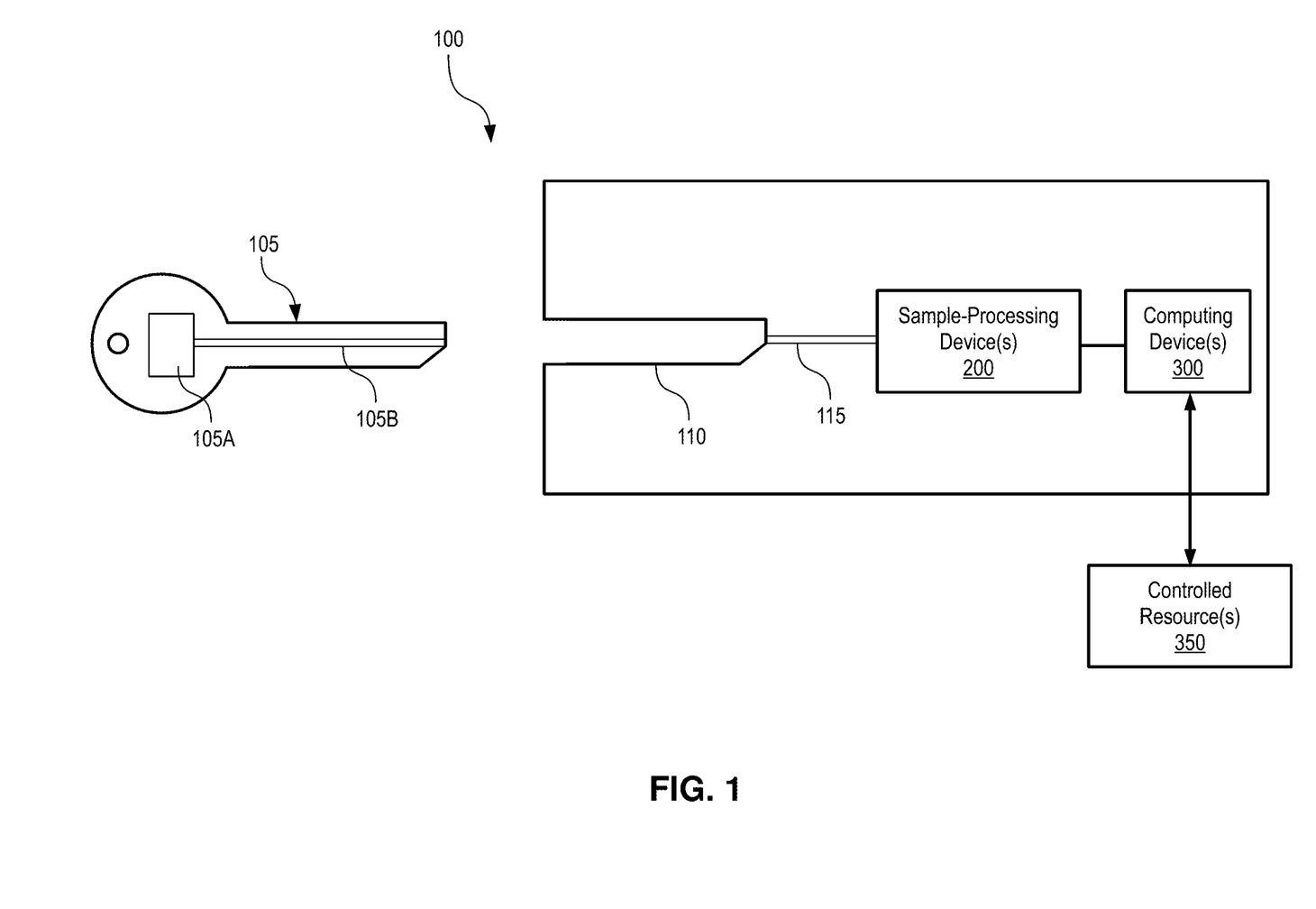
FIG. 1 illustrates an example biochemically-enabled/electrochemically-enabled security system, according to some embodiments.

FIG. 1 illustrates an example security system. System 100 comprises a receptacle 110, one or more sample-processing devices 200, and one or more computing devices 300. A key 105 is configured to deliver a biological sample to receptacle 110. The biological sample is a portion of biological material that is stored within a microfluid chamber 105A, which is disposed within key 105. In some embodiments, the biological material comprises DNA oligos that are synthesized, manufactured, and/or otherwise encoded in accordance with the techniques described herein.

Receptacle 110 is configured to receive the biological sample from key 105. For example, receptacle 110 may comprise a receptor module that is configured to extract the biological sample from container 105A through conduit 105B of key 105, and then to pass the extracted biological sample through conduit 115 to sample-processing device(s) 200. In various embodiments, the receptor module may extract the biological sample through various mechanical, electrical, and/or electro-mechanical means. By way of example, the transfer of biological sample from the key to through the receptacle to the sample-processing device could be done via capillary effect or in a pressurized manner (e.g., by using a micro-lever). In various embodiments, the receptacle may be integrated within the sample-processing device, thereby obviating the need for a conduit.

A sample-processing device 200 is configured to process the biological sample received through receptacle 110 and to determine one or more properties of the sample. According to the techniques described herein, sample-processing device(s) 200 send to computing device(s) 300 information that represents the one or more properties of the biological sample. For example, in some embodiments a DNA sequencer within sample-processing system 200 may sequence one or more target oligos that are comprised in the sample to determine the DNA sequence of the oligos. The read sequence may then be passed to computing device(s) 300 for further processing. In another example, a biochemical device may determine one or more chemical properties of the sample according to the techniques described herein, and to pass information about the properties to computing device(s) 300.

Computing device(s) 300 are configured to receive information from sample-processing device(s) 200, where the received information may comprise data in a suitable format. Computing device(s) 300 may process the received information in order to control access to one or more resources 350. For example, in one embodiment the resource being controlled may be a bank vault, a deposit box, or some other individually secured container that is used to store valuables. In another embodiment, the resource being controlled may be a file, an electronic document, a peripheral device, or another computing device that stores valuable information. According to the techniques described herein, computing device(s) 300 make a decision whether to grant or deny access to the controlled resource(s) 350 based on the information received from the sample-processing device(s) 200. By way of example, computing device(s) 300 may compare the set of read sequences (RS) acquired from the biological sample to the sets of expected sequences (ES) for all keys issued for system 300. If the set of RS for the biological sample from key 105 match (or otherwise satisfy other equivalency criteria for) a given set of ES, then computing device(s) 300 would grant access to the resource 350 requested by key 105; otherwise, computing device(s) 300 would deny access to the requested resource. In some embodiments, the controlled resource may be a replicate security system that itself includes one or more sample-processing devices and/or computing devices.

Figure 2:
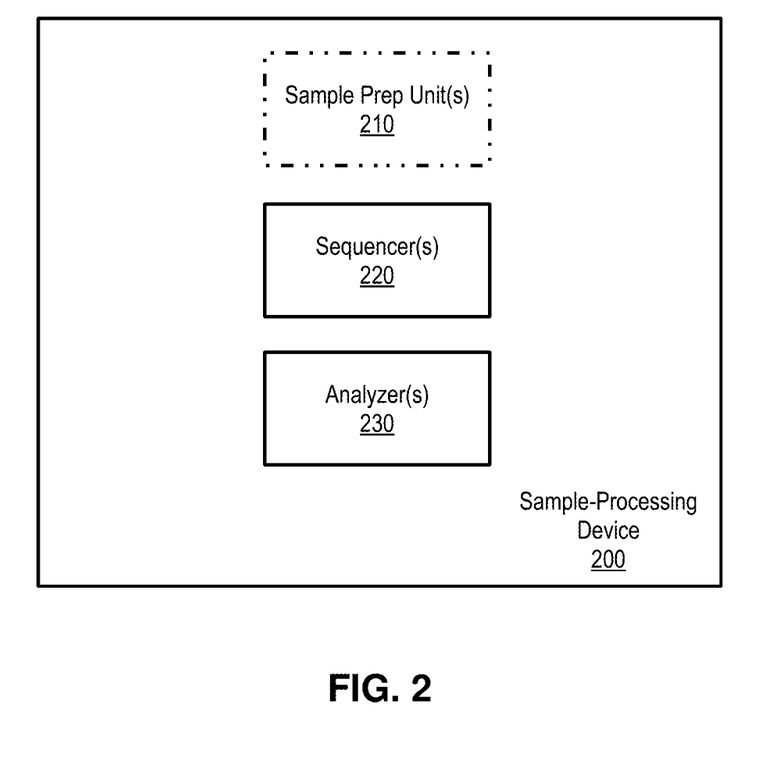
FIG. 2 illustrates an example sample-processing device, according to some embodiments.

FIG. 2 illustrates an example sample-processing device. In various embodiments, a sample-processing device may comprise one or more DNA sequencers 220 and/or one or more biochemical analyzers 230. Optionally, some embodiments may also include one or more sample prep unit(s) 210 that are configured to perform any necessary biochemical transformations—e.g., such as library preparation for, or based on, the biological sample received from the DNA key.

In some embodiments a DNA sequencer 220 is configured to sequence a received oligo to determine a set of reads that represents the DNA sequence of the oligo. Sequencer 220 may then determine the exact sequence of DNA bases represented in the set of reads by performing various data processing operations. Alternatively, after obtaining the set of reads, sequencer 220 may pass the raw reads to a computing device for further processing. After these operations by sequencer 220, a set of read sequences (RS) is obtained to correspond to the biological sample received from the DNA key. In some embodiments, a sample-processing device 200 may include a biochemical analyzer 230. Analyzer 230 is configured to determine one or more chemical or biochemical properties of the sample received from the key, and to generate information that represents these properties. Thereafter, analyzer 230 may send the generated information to a computing device for further processing.

Figure 3:
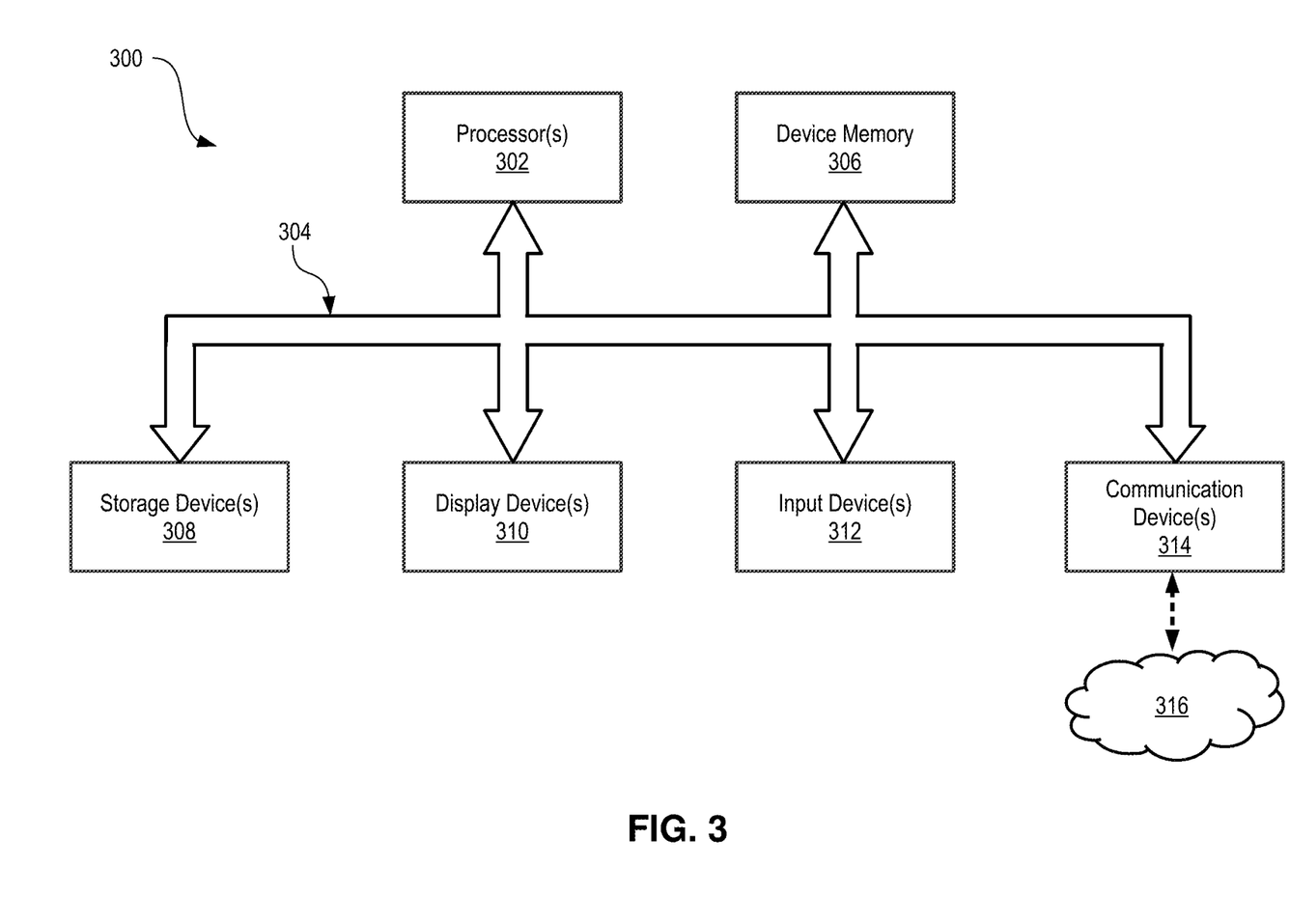
FIG. 3 illustrates an example computing device, according to some embodiments.

FIG. 3 illustrates an example computing device. Computing device 300 includes, but is not limited to, one or more processors 302 operationally coupled to device memory 306 over one or more buses such as bus 304. Depending on specific implementations and form factors, computing device 300 may also include storage device(s) 308, display device(s) 310, input device(s) 312, and communication device(s) 314.

A processor 302 is a hardware device configured to execute sequences of instructions in order to perform various operations such as, for example, arithmetical, logical, and input/output operations. A typical example of a processor is a central processing unit (CPU), but it is noted that other types of processors such as vector processors and array processors can perform similar operations. Examples of hardware devices that can operate as processors include, but are not limited to, microprocessors, microcontrollers, digital signal processors (DSPs), systems-on-chip, and the like. Processor 302 is configured to receive executable instructions over one or more data and/or address buses such as bus 304. Bus 304 is configured to couple various device components, including memory 306, to processor(s) 302. Bus 304 may include one or more bus structures (e.g., such as a memory bus or memory controller, a peripheral bus, and a local bus) that may have any of a variety of bus architectures. Device memory 306 is configured to store data and executable instructions for processor(s) 302. Device memory 306 may include volatile and/or non-volatile memory such as read-only memory (ROM) and random-access memory (RAM). For example, a basic input/output system (BIOS) containing the basic executable instructions for transferring information between device components (e.g., during start-up) is typically stored in ROM. RAM typically stores data and executable instructions that are immediately accessible and/or being operated on by processor(s) 302 during execution. Device memory 306 is an example of non-transitory computer-readable medium.

Computer-readable media may include any available medium that can be accessed by a computing device (and/or the processors thereof) and includes both volatile and non-volatile media and removable and non-removable media. One example of non-transitory computer-readable media is storage media. Storage media includes media implemented in any method or technology for storage of information such as computer-readable instructions, data structures, program modules, and/or other data. Examples of storage media include, but are not limited to, RAM, ROM, electrically erasable programmable read-only memory (EEPROM), removable memory such as flash memory and solid state drives (SSD), compact-disk read-only memory (CD-ROM), digital versatile disks (DVD) and other optical disks, magnetic cassettes, magnetic tapes, magnetic disks or other magnetic storage devices, electromagnetic disks, and any other medium which can be used to store the desired information and which can be accessed and read by a computing device. Another example of computer-readable media is communication media. Communication media typically embody computer-readable instructions, data structures, program modules, or other data, in a modulated data signal such as a carrier wave or other transport mechanism and includes any information delivery media. By way of example, and not limitation, communication media includes wired media such as a wired network or direct-wired connection, and wireless media such as acoustic, radio frequency (RF), infrared and other wireless media.

Computing device 300 may include, and/or have access to, various non-transitory computer-readable media that is embodied in one or more storage devices 308. Storage device(s) 308 may be coupled to processors(s) 302 over one or more buses such as bus 304. Storage device(s) 308 are configured to provide persistent storage of executable and other computer-readable instructions, data structures, program modules, and other data for computing device 300 and/or for its users. In various embodiments and form factors of computing device 300, storage device(s) 308 may include persistent storage media of one or more types including, but not limited to, electromagnetic disks (e.g., hard disks), optical storage disks (e.g., DVDs and CD-ROMs), magneto-optical storage disks, solid-state drives, flash memory cards, universal serial bus (USB) flash drives, and the like. By way of example, storage device(s) 308 may include a hard disk drive that stores the executable instructions of an Operating System (OS) for computing device 300, the executable instructions of one or more computer programs, clients, and other computer processes that can be executed on the computing device, and any OS and/or user data in various formats.

Computing device 300 may also include one or more display devices 310 and one or more input devices 312 that are coupled to processor(s) 302 over one or more buses such as bus 304. Display device(s) 310 may include any devices configured to receive information from, and/or present information to, user(s) of computing device 300. Examples of such display devices include, but are not limited to, cathode-ray tube (CRT) monitors, liquid crystal displays (LCDs), light emitting diode (LED) displays, field emission (FED, or "flat panel" CRT) displays, plasma displays, electro-luminescent displays, and any other types of display devices. Input device(s) 312 may include a general pointing device (e.g., such as a computer mouse, a trackpad, or an equivalent spatial-input device), an alphanumeric input device (e.g., such as a keyboard), and/or any other suitable human interface device (HID) that can communicate commands and other user-generated information to processor(s) 302.

Computing device 300 may include one or more communication devices 314 that are coupled to processor(s) 302 over one or more buses such as bus 304. Communication device(s) 314 are configured to receive and transmit data from and to other devices and computers. For example, communication device(s) 314 may include one or more USB controllers for communicating with USB peripheral devices, one or more network storage controllers for communicating with storage area network (SAN) devices and/or network-attached storage (NAS) devices, one or more network interface cards (NICs) for communicating over wired communication networks, and/or one or more wireless network cards for communicating over a variety of wireless data-transmission protocols such as, for example, IEEE 802.11 and/or Bluetooth. Using communication device(s) 314, computing device 300 may operate in a networked environment using logical and/or physical connections to one or more remote computing devices and computers. For example, computing device 300 may be connected to one or more remote computers that provide access to block-level data storage over a SAN protocol and/or to file-level data storage over a NAS protocol. In another example, computing device 300 may be connected to one or more networks 316 over connections that support one or more networking protocols. Network(s) 316 may include, without limitation, a local area network (LAN), a wide area network (WAN), a global network (e.g., the Internet), and/or any other type of network or combination of networks.

Some embodiments of the techniques described herein may be implemented as a computer program product that may include sequences of instructions stored on non-transitory computer-readable media. These instructions may be used to program one or more computing devices that include one or more special-purpose or general-purpose processors (e.g., CPUs) or equivalents thereof (e.g., such as processing engines, processing cores, etc). When executed by the processor(s), the sequences of instructions cause the computing device(s) to perform the operations (e.g., to control one or more of DNA oligo synthesis, sample processing, DNA sequencing, access to resources, etc.) according to some of the embodiments of the techniques described herein. Additionally or instead of, some embodiments of the techniques described herein may be practiced in distributed computing environments that may involve more than one computing device. One example of a distributed computing environment is a client-server environment, in which some of the various functions of the techniques described herein may be performed by a client program product executing on a computing device and some of the functions may be performed by a server program product executing on a server computer. Another example of a distributed computing environment is a cloud computing environment. In a cloud computing environment, computing resources are provided and delivered as a service over a network such as a local-area network (e.g., LAN) or a wide-area network (e.g., the Internet). Examples of cloud-based computing resources may include, without limitation: physical infrastructure resources (e.g., physical computing devices or computer systems, and virtual machines executing thereon) that are allocated on-demand to perform particular tasks and functions; platform infrastructure resources (e.g., an OS, programming language execution environments, database servers, web servers, etc.) that are installed/imaged on-demand onto the allocated physical infrastructure resources; and application software resources (e.g., application servers, single-tenant and multi-tenant software platforms, etc.) that are instantiated and executed on-demand in the environment provided by the platform infrastructure resources. Another example of a distributed computing environment is a computing cluster environment, in which multiple computing devices each with its own OS instance are connected over a fast local network. Another example of a distributed computing environment is a grid computing environment in which multiple, possibly heterogeneous and/or geographically dispersed, computing devices are connected over conventional network(s) to perform a common task or goal. In various distributed computing environments, the information transferred between the various computing devices may be pulled or pushed across the transmission medium that connects the computing devices.

Figure 4:
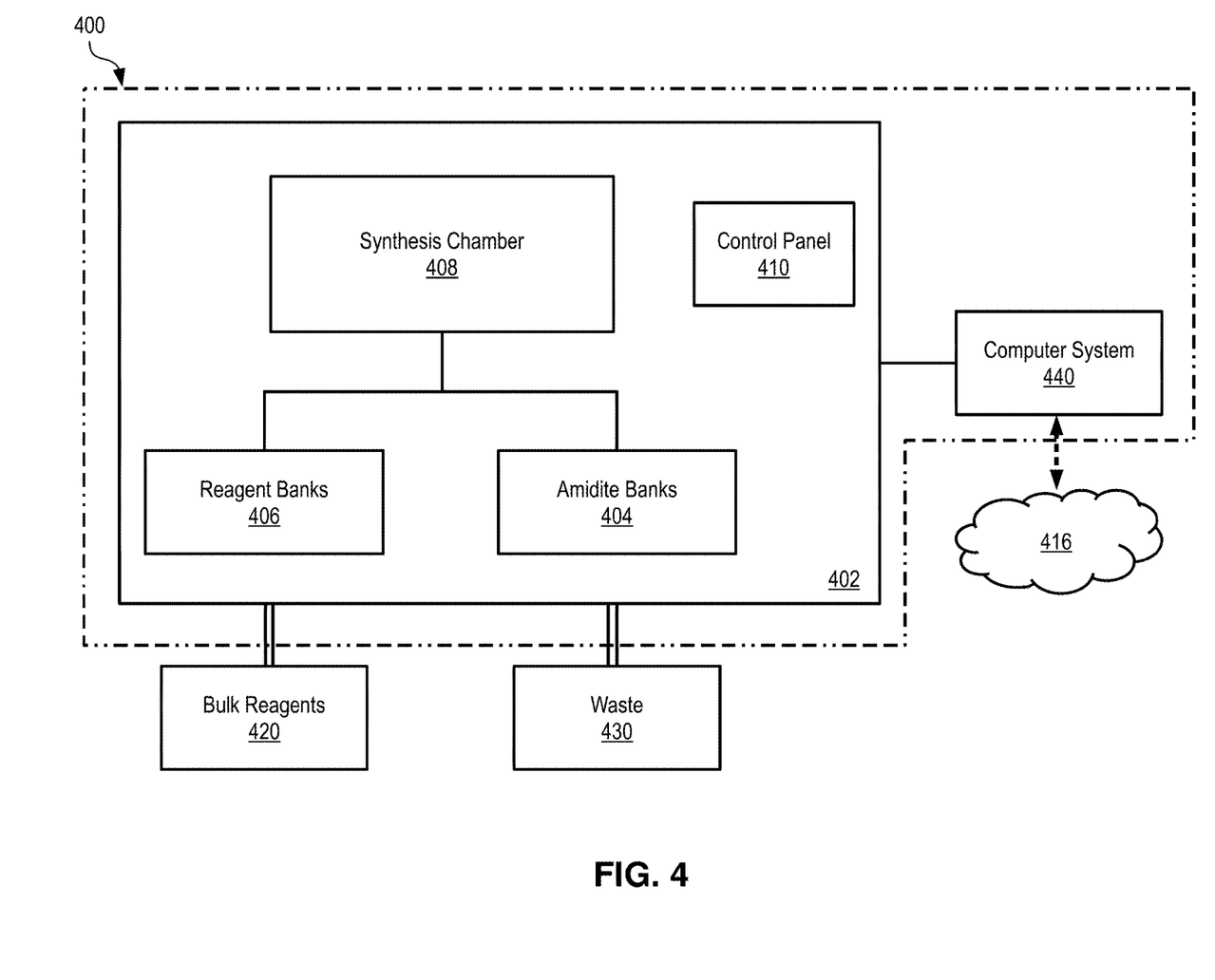
FIG. 4 illustrates an example deoxyribonucleic acid (DNA) oligonucleotide synthesizer system, according to some embodiments.

FIG. 4 illustrates an example synthesizer system 400 which may be used by the techniques and methods described herein to encode sequences assigned to DNA keys into DNA oligos. In some embodiments, oligo synthesizer system 400 may be a high throughput, large scale instrument capable of simultaneously synthesizing up to 48, 92, 192 oligos (or more) in quantities that may range from 2 μMole to several MilliMoles. Oligo synthesizer system 400 is configured to facilitate the joining of single nucleotides (or bases) to form oligos having user-specified sequences. Examples of such oligo synthesizer system include the ABI3900 High-Throughput DNA Synthesizer and Agilent's Oligo Library Synthesis microarray platform (SurePrint), but it is noted that various oligo synthesizer systems available on the market may be suitable for implementing the techniques described herein.

Oligo synthesizer system 400 includes a synthesizer 402 that is communicatively and/or operatively coupled to computer system 440. Synthesizer 402 includes amidite banks 404, reagent banks 406, synthesis chamber 408, and control panel 410. Various fluidic lines, tubing, valves, and other fluidic connections may be used to connect amidite banks 404 and reagent banks 406 to synthesis chamber 408. Amidite banks 404 may be bottles or other containers that store amidates (e.g., such as phoramidites) for the each of the bases "A", "C", "G", "T", "U" and other bases (e.g., inosine or synthetic/unnatural bases) that may be used. Reagent banks 406 are used to store various reagents, chemicals, and dyes that are needed during oligo synthesis. For example, reagent banks 406 may be bottles or other containers that store various solutions and mixtures such as, for example, tetrazole-acetonitrile, 1-methylimidazole-tetrahydrofuran, acetic anhydride-pyridine, iodine-pyridine, etc.

Synthesis chamber 408 is configured to receive solid support structure(s) in which oligos are generated. In some embodiments, the solid support structure may be a cartridge (or plate) with columns, where a column may be a vial that is specifically designed to work with the particular synthesizer system. For example, the cartridge/plate may be designed to hold a number of columns (e.g., 48, 96, 192, etc.), each of which may be used to produce a different oligo within the same cycle. Each column may be prepped prior to oligo synthesis, e.g., by being provided with a first base of an oligo sequence linked to some solid support or bead disposed in the column. In some embodiments, the solid support structure may be a microarray that is designed for in situ synthesis process that "prints" oligos base-by-base. For example, an inkjet-like printing process may be used to deposit nucleotide/oligo monomers onto specific spots in the microarrays, which enables the accurate delivery of small volumes (e.g., picoliters) of the amidites, reagents and other chemicals needed to generate the oligos. Synthesis chamber 408 may also include robotic arms, rails, sleeves or other suitable mechanical and/or electro-mechanical components that are configured to position the dispense tips or nozzles with respect to the solid support structure(s) (e.g., cartridges, microarrays, etc.), wash lines, and waste lines in order to receive and drain amidates, reagents, chemicals, and other fluids during the oligo generation cycles. Control panel 410 may include various buttons, pressure gauges, and control elements that allow a user to operate synthesizer 402.

In some embodiments, synthesizer 402 may be in fluidic connection with bulk reagent containers 420 and waste containers 430. Bulk reagent containers 420 may be bottles or other containers that store various chemicals used during operation. For example, a bulk container 420 may be used to store argon or other inert material that is used to flush the fluidic lines and the columns used in synthesis chamber 408. Waste containers 430 may be bottles or other suitable containers that are used to store any waste fluids that are pumped, drained, or otherwise transferred out of synthesis chamber 408. Synthesizer 402 may also include various other components such as motors, sensors, valves, connectors, etc., that are configured to pump fluids in and out of the various components of the synthesizer.

Computer system 440 is a suitable computing device and may be communicatively coupled to a network 416. Examples of such computer system and network are described above with respect to FIG. 3, but it is noted that any suitable computer system (e.g., a personal system or an embedded system) may be used to implement various aspects of the techniques described herein. Referring to FIG. 4, computer system 440 is configured to execute software programs that control the operation of synthesizer 402 to generate oligos in accordance with the techniques described herein. For example, computer system 440 may be configured with a suitable software program or application that provides a graphical user interface for entry of information about the oligos that need to be generated by synthesizer system 400. Through the user interface, a user may enter or otherwise specify the sequences assigned to a particular DNA key and/or a path to file(s) which store the desired sequences and any other instructions relevant to encoding the sequences into DNA oligos.

In operation, synthesizer system 400 may use a cycle-based protocol to generate oligos having DNA sequences that are entered by a user or are specified in files (or other suitable data structures) accessible by computer system 440. A cycle may be specified by instructions stored in file(s) or other suitable data structure(s), which instructions control and direct synthesizer 402 what steps to perform during the generation of an oligo in a given cartridge column or a given a microarray spot. A series of cycles may be programmed by using suitable software that is executed in computer system 440. In order to incorporate a nucleotide base into a growing oligo, during a cycle a synthesizer may perform a series of steps by applying the appropriate amidites, reagents, and other chemicals on a cartridge column or a microarray spot. Depending on the various types of synthesis, such steps may include: a de-blocking step that produces a free 5'-terminal hydroxyl group in the growing oligos; a coupling step that applies an amidite with the desired base to the free 5'-terminal hydroxyl group; a capping step that applies an appropriate reagent to block any unreacted 5'-terminal hydroxyl groups in the growing oligos; an oxidation step that applies an appropriate (e.g., iodine-based) solution to cap any newly-formed phosphate linkages of the growing oligos; a protection step that applies the appropriate reagent(s) to complete the nucleotide chains of the growing oligos; and a cleaving step that applies the appropriate reagent(s) to cleave the generated oligos from their solid support structure(s) and/or to transfer the oligos in appropriate vials. According to the techniques described herein, computer system 440 and the software executing thereon control and direct synthesizer 402 to generate a set of DNA oligos that represent the sequences assigned to a DNA key.

In an example security mechanism according to the techniques described herein, a bank (or other key-issuing institution) may order a set of DNA oligos from a lab that is proficient and/or certified in DNA synthesis. Alternatively, in order to increase security, the bank (or other key-issuing institution) may purchase and operate DNA synthesizer systems as described heretofore. In any case, after the set of sequences representing the code for a DNA key are designed, the set of sequences is synthesized into a set of DNA oligos. A DNA solution to fill the key is then prepared and transferred into the physical device (key). For example, the DNA solution may be prepared from the synthesized DNA oligos by mixing them in the desired proportions. In addition, an amount of the prepared DNA solution may be stored securely by the key-issuing institution for comparison and other purposes. An amount of the prepared DNA solution is then transferred into the physical key—e.g., via pressurized inlets of the key or other suitable conduits.

Figure 5:
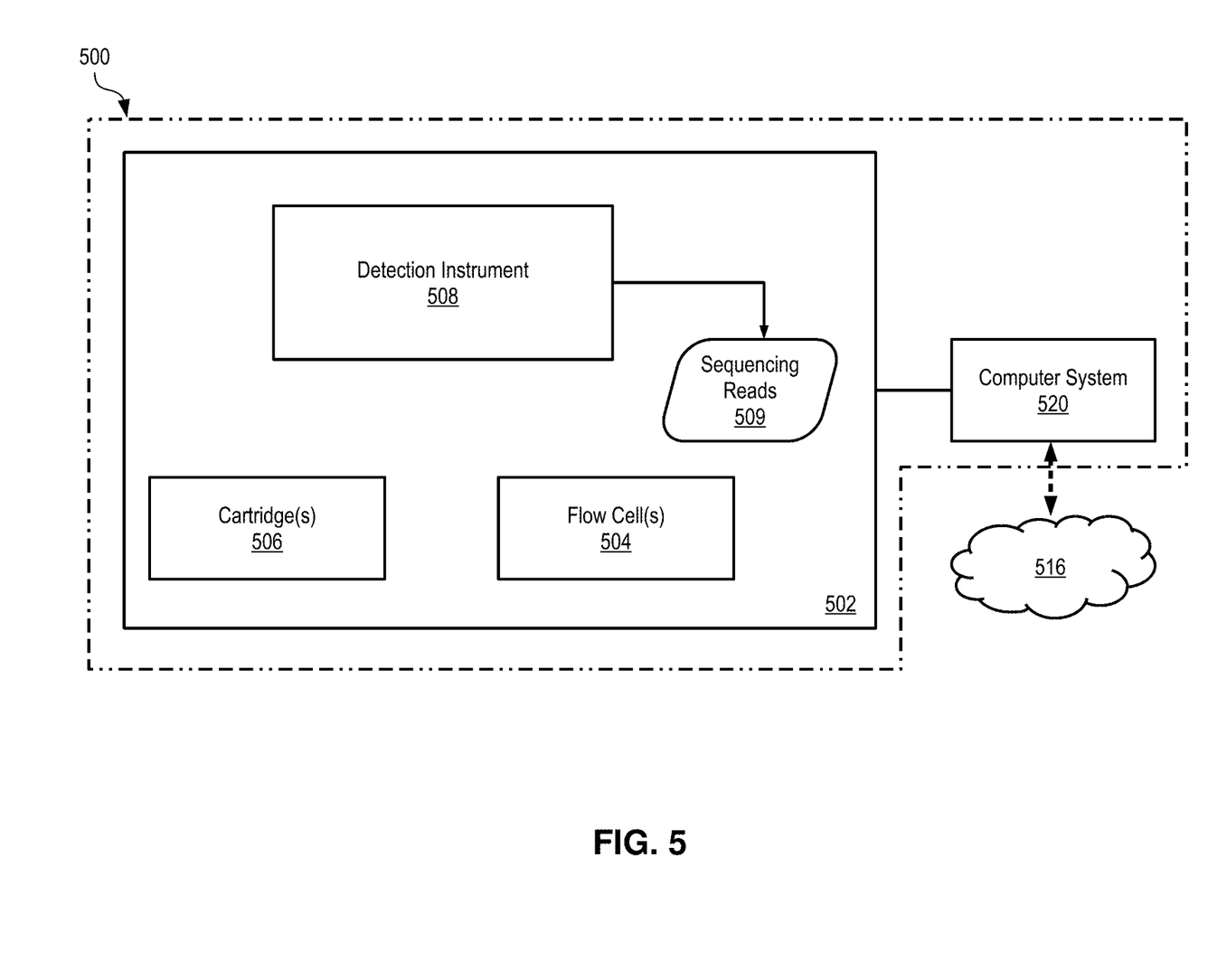
FIG. 5 illustrates an example DNA sequencer system, according to some embodiments.

FIG. 5 illustrates an example DNA sequencing system 500 which may be used to implement the techniques and methods described herein to sequence DNA oligos acquired from a biological sample received from a DNA key. In some embodiments, DNA sequencing system 500 may be a high throughput instrument capable of sequencing oligos by using any suitable next generation sequencing (NGS) technology. Examples of such DNA sequencing systems include, without limitation, the MiSeq, HiSeq and NextSeq sequencers manufactured by Illumina, Inc., and Ion Proton systems manufactured by Life Technologies, Inc. It is noted, however, that various other commercial DNA sequencing systems may be suitable for implementing the techniques described herein.

For example, DNA sequencing systems provided by Illumina, Inc. are fluorescent-based, and due to the relatively long processing time (e.g., ~5 minutes per cycle of sequencing) may not be appropriate for implementing the herein-described security mechanisms as a real-time system that requires extremely high turn-around times (e.g., such as a few minutes). However, fluorescent-based DNA sequencing systems may be useful and very practical for security contexts that do not require high turn-around times. Also, as DNA sequencing technology advances, the acquisition time per cycle of various sequencing systems is generally improved (e.g., from minutes to seconds), thereby making such sequencing systems more useful and practical for implementing the biochemically-enabled security mechanisms described herein. Currently, electronic-based DNA sequencing systems (which have very fast signal/date acquisition rates) are appropriate and practical for security systems that require short turn-around times. One example of such electronic-based DNA sequencing systems is the Ion Torrent family of sequencers provided by Life Technologies, Inc. (now Thermo Fisher Scientific). Further, at least one electronic-based DNA sequencing system that operates based on nanopore technology is in the last stage of development (e.g., a family of sequencing devices developed by Oxford Nanopore Technologies). As fast acquisition time is essential in establishing a quick transaction between acquiring the information in a DNA key and verifying/validating the acquired information against the security information stored at the key-processing institution (e.g., such as bank), nanopore-based sequencing technologies have a great promise for rapid readout and thus are particularly useful for implementing the security mechanisms described herein.

Referring to FIG. 5, DNA sequencing system 500 includes a sequencing device (sequencer) 502 that is communicatively and/or operatively coupled to computer system 520. Sequencer 502 includes compartments that can accept flow cell(s) or slides 504 with the oligos being sequenced (target oligos), cartridge(s) 506 with the sequencing reagents and buffers used during sequencing, and detection instrument 508 which performs the sequencing. Various fluidic lines, tubing, valves, and other fluidic connections may be used to connect the compartments with flow cell(s) or slides 504 and cartridge(s) 506 to detection instrument 508. A flow cell 504 may include a housing that encloses a solid support (e.g., a microarray, a chip, beads, etc.), with one or more ports being provided for loading the target oligos into the flow cell and for administering the various reagents and buffers during sequencing cycles. In some sequencing systems, the target oligos may be pre-processed into libraries by applying thereto various chemical steps such as denaturing, diluting, etc. A cartridge 506 is used to store various sequencing reagents, buffers, chemicals, as well as any waste that are needed or produced during sequencing. For example, a cartridge 506 may include suitable storage reservoirs that store denaturation agents (e.g., formamide), wash solutions, probes, etc.

Detection instrument 508 is configured to detect the DNA sequences of the target oligos and to generate raw reads 509. In various embodiments, detection instrument 508 may utilize various sequencing mechanisms such as, for example, sequencing by synthesis, sequencing by ligation, sequencing by hybridization, etc., where such mechanisms may be employed in massively-parallel fashion in order to increase throughput. Further, in various embodiments detection instrument 508 may detect the DNA bases of the target oligos by using optical-based detection, semiconductor-based (or electronic) detection, electrical-based (e.g., nanopore) detection, etc. In various embodiments, detection instrument 508 may also include various suitable mechanical and/or electro-mechanical components that may be configured to position the flow cell 504 at the beginning and/or during sequencing.

Computer system 520 is a suitable computing device and may be communicatively coupled to a network 516. Examples of such computer system and network are described above with respect to FIG. 3. Referring to FIG. 5, computer system 520 is configured to execute software programs that control the operation of sequencer 502 to generate the reads 509 that represent the DNA sequences of the target oligos, in accordance with the techniques described herein. For example, computer system 520 may be configured with suitable software program(s) or application(s) that control the various sequencing cycles performed by sequencer 502. In addition, in some embodiments computer system 520 may be further configured to perform various post-sequencing steps in accordance with the techniques described herein such as, for example, performing error detection/correction on reads 509, assembling longer reads from the generated reads 509, etc.

In operation, computer system 520 controls the operation of DNA sequencing system 500. Sequencing system 500 is first loaded with flow cell(s) or slides 504 that contain the target oligos and with the sequencing cartridge(s) 506. According to the techniques described herein, the target oligos are acquired from a biological sample that is received/extracted from a DNA key. Prior to and/or after loading the flow cells/slides, the target oligos may be amplified (e.g., by using polymerase chain reaction, PCR) in order to preserve a sufficient amount for each read. Then, sequencing system 500 performs its sequencing cycles and generates sequencing reads 509 that represent the DNA sequences of the target oligos. A read is generally a sequence of data values that represent (fully or partially) the DNA sequence of a corresponding target oligo. Depending on the processing software used by the sequencing system, in some implementations the reads 509 may be further assembled into longer read sequences that represent the information encoded in the target oligos.

Computer system 520 and the software executing thereon may then perform the steps and operations of the decoding mechanism described herein. For example, in some embodiments, computer system 520 and the software executing thereon may bin the set of read sequences (RS), which represent the DNA oligos of the received DNA key, to obtain a set of filtered sequences (FS). The computer system 520 and the software executing thereon then compares the set of FS to the superset of the sets of expected sequences (ES) for the issued keys, in order to determine whether the set of FS represents a valid key. If the computer system 520 and the software executing thereon find a match (or other predefined equivalency) between any set of ES and the set of FS that represents the presented DNA key, then a determination is made that the presented DNA key is valid and access to the resource requested with the key is granted. Otherwise, if the set of FS does not match any of the sets of ES, access to the requested resource is denied.

Example 1

Method for Encoding a DNA Key

Figure 6:
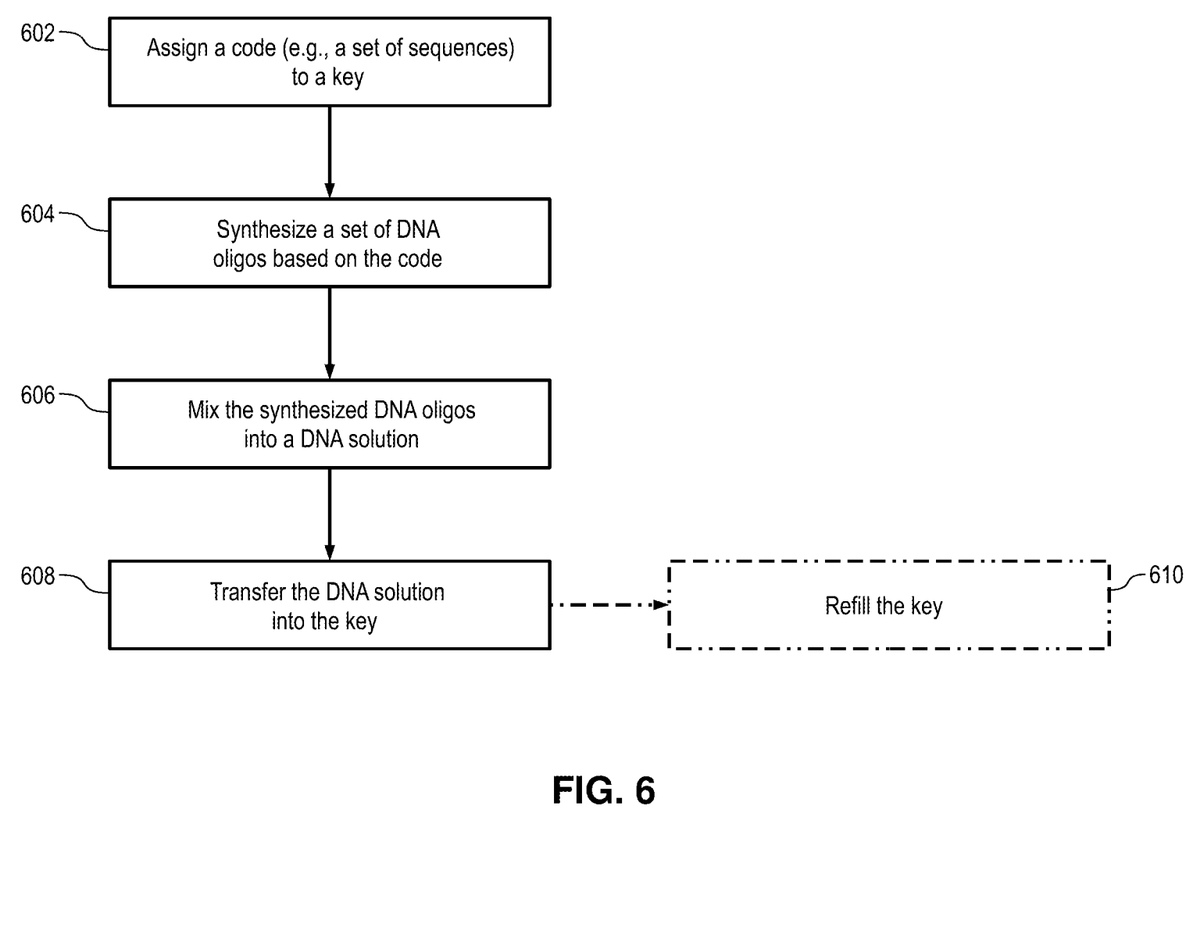
FIG. 6 illustrates an example method for encoding a DNA key, according to some embodiments.

FIG. 6 is a flow diagram illustrating an example method for encoding a DNA key. The steps of the method in FIG. 6 are described as being performed, at least partially, by a DNA synthesizer system. It is noted, however, that various implementations and embodiments may use various, and possibly different, systems to perform the steps of the method in FIG. 6. For example, in various embodiments a DNA-key enabled system may be configured with software instructions which, when executed by one or more processors, are operable to control and instruct one or more systems (or components thereof) to perform the steps of the method in FIG. 6 automatically and without user intervention. In another example, in various embodiments the steps of the method in FIG. 6, and/or any operations thereof, may be performed by multiple different systems that may or may not operate under common control. Thus, the description hereinafter of the method in FIG. 6 is to be regarded in an illustrative rather than a restrictive sense.

Referring to FIG. 6, in step 602 a code is assigned to a key in a design phase. The code is a set of DNA sequences that may be generated manually, automatically, or in any suitable combination thereof that allows for generating secure information. For example, in some embodiments the DNA sequences comprised in a code may be manually selected from a predefined table by a user. In another example, the DNA sequences may be automatically generated by a computer system in a random or pseudo-random manner (where the computer system may or may not be configured to exclude any difficult-to-synthesize sequences). As part of the design phase, the set of DNA sequences assigned to the key may be stored in a security system as the set of expected sequences for the key. Further, as part of the design phase, error detection and/or error correction codes may also be designed into the structure of the DNA sequences assigned to the key. For example, such error detection/correction codes may be specific sequences of bases that allow for detecting/correcting errors in read sequences obtained by DNA sequencing of DNA oligos.

In step 604, a set of DNA oligos is synthesized based on the set of DNA sequences that comprise the code assigned to the key. For example, a DNA synthesizer system may generate (as described heretofore) a set of DNA oligos that represent the sequences assigned to the key.

In step 606, the synthesized set of DNA oligos are mixed into a DNA solution that represents the code for the key in a biochemical form. For example, standard lab equipment may be used (e.g., manually and/or automatically) to mix the synthesized DNA oligos in the desired proportions. Alternatively, in some embodiments the synthesized DNA oligos may be provided to the user/owner of the key in suitable containers (e.g., tubes, vials, etc.), with instructions for the user/owner on how to mix the oligos on his/her own into the DNA solution for the key.

In step 608, the DNA solution is then transferred (e.g., injected) into the key. For example, standard lab equipment may be used (e.g., manually and/or automatically) to transfer into a microfluid chamber of the key an amount of the prepared DNA solution via pressurized inlets of the key or other suitable conduits.

In step 610, the key may be refilled with the DNA solution if needed. For example, when the DNA solution reaches a certain minimum in the key, an indicator (e.g., a marker on the microfluid chamber thereof) can make the user aware of the need to refill the key. Since minute amounts of DNA material is needed for DNA sequencing, it is possible to design keys with chambers that are large enough to store material for millions of uses, and therefore avoid the need for a refill.

Example 2

Method for Providing Secure Access

In an example operational context, a user/owner of a DNA key would present the key when requesting access to a resource controlled by a security system. For example, a bank customer may present his/her DNA key and request access to a deposit box. In order to determine whether to grant or deny the requested access, the security system may perform (or cause to be performed) the steps of the method in FIG. 7.

Figure 7:
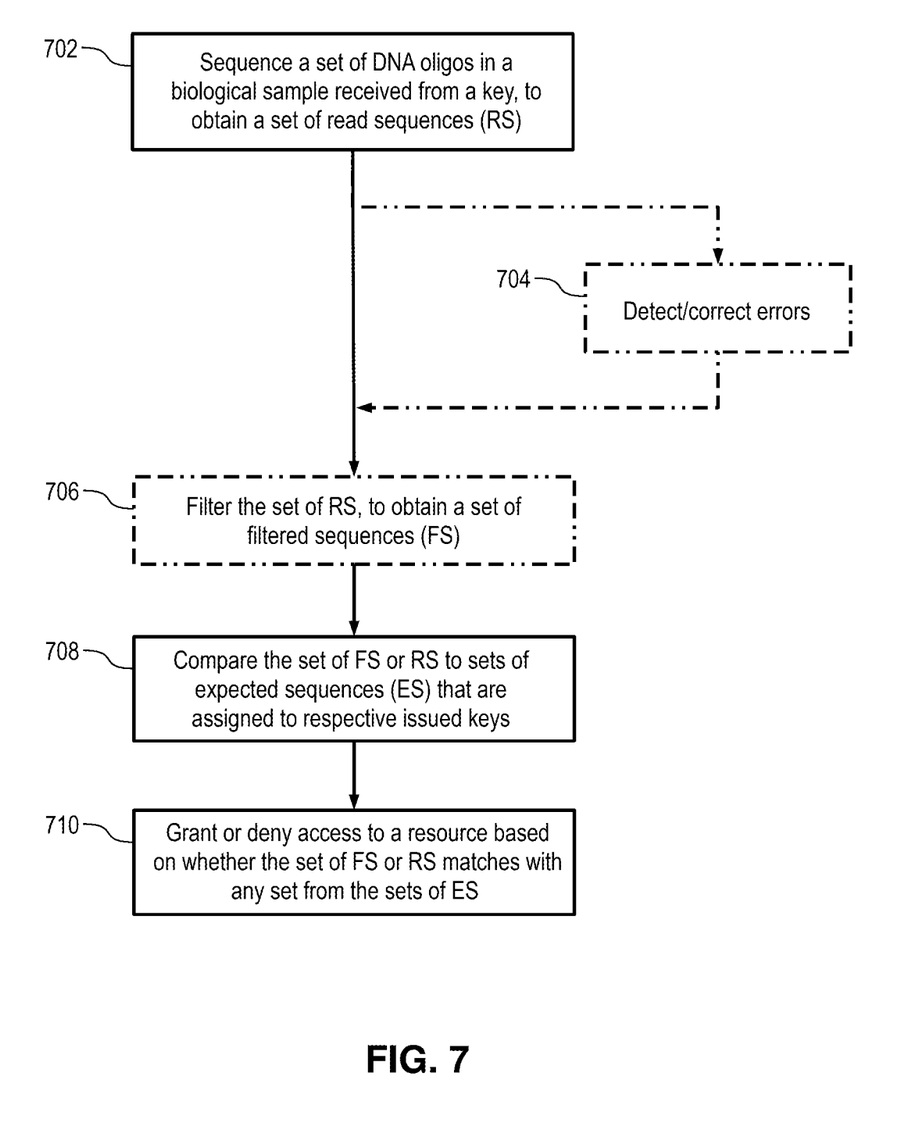
FIG. 7 illustrates an example method for providing secure access in a biochemically-enabled security system, according to some embodiments.

FIG. 7 is a flow diagram illustrating an example method for providing secure access in a biochemically-enabled security system, in accordance with the techniques described herein. The steps of the method in FIG. 7 are described as being performed, at least partially, by a DNA sequencing system and a computer system. It is noted, however, that various implementations and embodiments may use various, and possibly different, systems to perform the steps of the method in FIG. 7. For example, in various embodiments a DNA-key enabled system may be configured with software instructions which, when executed by one or more processors, are operable to control and instruct one or more systems (or components thereof) to perform the steps of the method in FIG. 7 automatically and without user intervention. In another example, in various embodiments the steps of the method in FIG. 7, and/or any operations thereof, may be performed by multiple different systems that may or may not operate under common control. Thus, the description hereinafter of the method in FIG. 7 is to be regarded in an illustrative rather than a restrictive sense.

Referring to FIG. 7, in step 702 a set of DNA oligos is sequenced to obtain a set of read sequences (RS), where the set of DNA oligos is contained in a biological sample received from a key. For example, a security system (and/or a sample-processing device thereof) may receive the biological sample through extraction or injection from the key. Prior to sequencing, the security system (or a subsystem thereof) may amplify the set of DNA oligos in the biological sample (e.g., by using PCR) in order to preserve a sufficient amount for sequencing. The resulting target DNA oligos are then provided to a DNA sequencer or sequencing system, which sequences the oligos to obtain the corresponding set of read sequences (RS).

If error detection/correction codes are included in the set of DNA oligos during encoding, then in step 704 such detection/correction can be used to detect/correct errors in the acquired read sequences. For example, a computer system may execute program(s) or other executable instructions (e.g., scripts) in order to determine whether there are any errors in the acquired read sequences that were caused during DNA synthesizing or DNA sequencing, and if so to correct any such errors.

In step 706, the set of read sequences (RS) is filtered to obtain a set of filtered sequences (FS), according to some embodiments. This provides effective immunity to noise that may be introduced in the set of RS because of synthesizing and/or sequencing errors. For example, a computer system may execute program(s) or other executable instructions (e.g., scripts) in order to bin the set of read sequences (RS)

into bins, where each bin is associated with the same read sequence. The bins with the highest counts of read sequences are then identified based on a threshold value. By way of example, the set of FS may include the read sequences from those bins whose counts exceed the threshold value.

In step 708, the set of FS is compared to sets of expected sequences (ES) that are assigned to respective keys issued in the security system. For example, the set of FS is compared with the sets of ES in order to determine whether the set of FS represents a valid key. In some embodiments, this comparison step may be performed by comparing the sets of ES with the set of RS instead of with the set of FS. To determine whether the DNA key presented to the security system is valid, a computer system may search the search space (e.g., all the sets of ES in the system) for a match between any set of ES and the set of FS/RS that represents the DNA key. In some embodiments, a match should be found for no more than one key—that is, the computer system would determine the key as valid when only one set from the sets of ES would be exactly equal to the set of FS/RS. In other embodiments, instead of using an exact match, the computer system would determine the key as valid when a given set of ES (from the search space) is found to be a subset of the set of FS/RS.

In step 710, access to the resource requested with the key is denied or granted based on whether the set of FS/RS matches with any set of ES. For example, if in step 708 the computer system determines that the set of FS/RS matches with a set of ES (e.g., the presented DNA key is valid), then in step 710 the computer system would grant access to the requested resource. Otherwise, if in step 708 the computer system determines that the set of FS/RS does not match with any set of ES (e.g., the presented DNA key is not valid), then in step 710 the computer system would deny access to the requested resource.

Although the steps and operations of the method(s) herein are shown and described in a particular order, in some embodiments the order of the steps and/or operations of each method may be altered so that certain steps and/or operations may be performed in an inverse order or so that certain step and/or operation may be performed, at least in part, concurrently and/or in parallel with other steps and/or operations. In other embodiments, sub-steps and/or sub-operations of distinct steps and/or operations may be performed in an intermittent and/or alternating manner.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative sense rather than a restrictive sense.

What is claimed is:

1. A method for controlling access to a resource, the method comprising:
   receiving a biological sample from a key, wherein the key comprises a fluid chamber that stores the biological sample, wherein the biological sample includes a set of deoxyribonucleic acid (DNA) oligos that are synthesized to represent a designed code assigned to the key;
   sequencing the set of DNA oligos to obtain a set of read sequences (RS);
   filtering the set of RS based on counts of sequences in the set of RS, to identify a set of filtered sequences (FS);
   comparing the set of FS to sets of expected sequences (ES), wherein the sets of ES are assigned to respective issued keys; and
   granting or denying access to the resource based on whether the set of FS matches with any set from the sets of ES.

2. The method of claim 1, further comprising performing error detection or error correction on the set of RS.

3. The method of claim 1, wherein filtering the set of RS comprises binning the set of RS into bins, wherein each bin has a respective count of sequences therein.

4. The method of claim 3, wherein filtering the set of RS further comprises identifying the set of FS based on those bins whose counts are greater than a threshold value.

5. The method of claim 1, wherein comparing the set of FS to the sets of ES comprises determining whether the set of FS is equal to at least one set of ES.

6. The method of claim 1, wherein comparing the set of FS to the sets of ES comprises determining whether at least one set of ES is a subset of the set of FS.

7. The method of claim 1, wherein the code assigned to the key is designed to include multiple sequences.

8. The method of claim 7, wherein the number of the multiple sequences is in a range between 2 and 2000, inclusive.

9. The method of claim 1, wherein the key is a master-key, and the set of DNA oligos represents M codes assigned to each of K keys, wherein M and K are numbers greater than 1.

10. The method of claim 9, wherein the set of RS includes M*K clusters of sequences, each cluster having a respective count of sequences therein.

11. The method of claim 10, further comprising validating the set of RS by computing a ratio between the counts of any two clusters.

12. The method of claim 10, further comprising validating the master-key, wherein validating the master-key comprises:
   comparing the count of each cluster to a first threshold value in order to determine valid sequences; and
   determining whether the master-key is valid by comparing the number of the valid sequences to a second threshold value.

13. The method of claim 10, further comprising validating the master-key, wherein validating the master-key comprises:
   computing a percent of impurity for the set of RS; and
   determining whether the master-key is valid by comparing the percent of impurity to a threshold value.

14. The method of claim 9, wherein M is equal to 3 and K is equal to 5.

15. The method of claim 1, wherein the code assigned to the key includes multiple sequences, and the set of DNA oligos is synthesized based on the multiple sequences.

16. The method of claim 1, wherein the code assigned to the key includes a password sequence, and the set of DNA oligos is synthesized to include an oligo representing the password sequence.

17. The method of claim 16, further comprising:
   determining whether the password sequence is included in the set of RS; and
   determining that the key is invalid when the password sequence is not included in the set of RS.

18. The method of claim 1, further comprising receiving and attempting to verify one or more of an electronic password, a fingerprint, and a retina scan, wherein sequencing the set of DNA oligos is performed only after or before the one or more of the electronic password, the fingerprint, and the retina scan are verified.

19. The method of claim 1, wherein the code assigned to the key includes multiple sequences derived from a genome of a human person.

20. The method of claim 1, further comprising:
applying a ligase to the biological sample in order to ligate oligos from the set of DNA oligos;
after sequencing the set of DNA oligos, determining the lengths of the sequences included in the set of RS; and
validating the set of DNA oligos based on the determined lengths.

* * * * *